US006849595B2

(12) United States Patent
Mark et al.

(10) Patent No.: US 6,849,595 B2
(45) Date of Patent: Feb. 1, 2005

(54) CALORICALLY DENSE NUTRITIONAL COMPOSITION

(75) Inventors: David A. Mark, Oak Park, IL (US); Diana Twyman, Chicago, IL (US); Tom Michalski, Grayslake, IL (US)

(73) Assignee: Nestec S.A., Vevey (CH)

(*) Notice: Subject to any disclaimer, the term of this patent is extended or adjusted under 35 U.S.C. 154(b) by 0 days.

(21) Appl. No.: 09/759,037

(22) Filed: Jan. 10, 2001

(65) Prior Publication Data

US 2001/0049352 A1 Dec. 6, 2001

Related U.S. Application Data

(63) Continuation of application No. 09/025,363, filed on Feb. 18, 1998.

(51) Int. Cl.$^7$ ......................... A61K 38/01; A61K 33/00
(52) U.S. Cl. ............................ 514/2; 514/21; 514/23; 514/547; 514/474; 514/494; 424/600; 424/641; 424/681; 426/72
(58) Field of Search ..................... 514/2, 494, 547, 514/21, 23, 474; 424/600, 702, 535, 641, 681; 426/72

(56) References Cited

U.S. PATENT DOCUMENTS

| | | |
|---|---|---|
| 4,112,123 A | 9/1978 | Roberts |
| 4,358,465 A | 11/1982 | Brule et al. |
| 4,361,587 A | 11/1982 | Brule et al. |
| 4,427,658 A | 1/1984 | Maubois et al. |
| 4,495,176 A | 1/1985 | Brule et al. |
| 4,670,268 A | 6/1987 | Mahmoud |
| 4,740,462 A | 4/1988 | Brule et al. |
| 4,753,963 A | 6/1988 | Jandacek et al. |
| 4,816,398 A | 3/1989 | Brule et al. |
| 4,920,098 A | 4/1990 | Cotter et al. |
| 4,931,300 A | 6/1990 | Monte |
| 4,980,450 A | 12/1990 | Brule et al. |
| 5,028,589 A | 7/1991 | Brule et al. |
| 5,053,387 A | 10/1991 | Alexander |
| 5,055,446 A | 10/1991 | Alexander et al. |
| 5,156,875 A | 10/1992 | Monte |
| 5,166,189 A | 11/1992 | Trimbo et al. |
| 5,221,668 A | 6/1993 | Henningfield et al. |
| 5,223,285 A | 6/1993 | DeMichele et al. |
| 5,260,279 A | 11/1993 | Greenberg |
| 5,340,603 A | 8/1994 | Neylan et al. |
| 5,422,127 A | 6/1995 | Dube et al. |
| 5,438,042 A | 8/1995 | Schmidl et al. |
| 5,480,872 A | 1/1996 | Cope et al. |
| 5,504,072 A | 4/1996 | Schmidl et al. |
| 5,547,927 A | 8/1996 | Cope et al. |
| 5,549,905 A | 8/1996 | Mark et al. |
| 5,574,065 A | 11/1996 | Trimbo |
| 5,589,468 A | 12/1996 | Lin et al. |
| 5,635,199 A | 6/1997 | Trimbo et al. |
| 5,661,123 A | 8/1997 | Stalker et al. |
| 5,700,782 A | 12/1997 | Cope et al. |
| 5,700,837 A | 12/1997 | Trimbo |
| 5,714,472 A | 2/1998 | Gray et al. |
| 5,723,446 A | 3/1998 | Gray et al. |
| 5,733,884 A | 3/1998 | Barbul et al. |
| 5,766,621 A | 6/1998 | Trimbo et al. |
| 6,200,950 B1 * | 3/2001 | Mark et al. ............... 514/2 |

FOREIGN PATENT DOCUMENTS

| | | |
|---|---|---|
| EP | 0 189 160 | 7/1986 |
| EP | 0 721 742 | 7/1996 |
| WO | 97/16079 | 5/1997 |

OTHER PUBLICATIONS

Brochure entitled "Respalor" by Mead Johnson & Company, 1994.

Brochure entitled "Pulmocare" by Ross Products Division, Abbott Laboratories, 1993.

Brochure entitled "Fresubin 750 MCT High–Caloric Formula for Oral and Tube Feeding" by Fresenius AG, 1989.

Culpepper–Morgan et al. article entitled "Using Enteral Nutrition Formulas" *The Gastroenterologist*, vol. 1, No. 2, Jun. 1993, pp. 143–156.

Ziegler et al. article entitled "Pharmacokinetic assessment of an oligopeptide–based enteral formula in abdominal surgery patients" *Am. J. Clin. Nutr.*, 1998 vol. 67, pp. 124–128.

Ziegler et al. article entitled "Present Knowledge in Nutrition" *International Live Sciences Institute*, 1996, pp. 38–40.

Alexander et al., "Beneficial Effects of Aggressive Protein Feeding in Severly Burned Children", Ann. Surg., vol. 192, No. 4, 1980, pp. 505–517.

Anderson et al., "Intestinal Protein Loss During Enteral Alimentation in Critically Ill Patients", J. Parenter Enteral Nutr., vol. 14 (Suppl), No. 1, 1990, p. 24, Abstract.

August et al., "Determination of Zinc and Copper Absorption at Three Dietary Zn–Cu Ratios by Using Stable Isotope Methods in Young Adult and Elderly Subjects", Am. J. Clin. Nutr., vol. 50, 1989, pp. 1457–1463.

Austin, "Water: Guidelines for Nutritional Support", Nutritional Support Services, vol. 6, No. 9, 1986, pp. 27–29.

Belcher et al., "Determinants of Urinary Nitrogen Excretion in Burned Patients", Burns, vol. 14, No. 4, 1988, pp 303–307.

(List continued on next page.)

*Primary Examiner*—Russell Travers
*Assistant Examiner*—Shahnam Sharareh
(74) *Attorney, Agent, or Firm*—Bell, Boyd & Lloyd LLC

(57) ABSTRACT

The present invention provides an enteral composition and method for providing nutrition to metabolically stressed patients. Pursuant to the present invention, the enteral composition has an increased caloric density of approximately 1.4 to 1.8 kcal/mL. The enteral composition includes a peptide based protein source, a lipid source, and a carbohydrate source.

17 Claims, No Drawings

OTHER PUBLICATIONS

Bell et al., "Alternative lipid sources for enteral and parenteral nutrition: Long– and medium– chain triglycerides, structured triglycerides, and fish oils", J. of the American Dietetic Association, vol. 91, No. 1, 1991, pp 74–78.

Bjerve et al., "Alpha–Linoleic Acid Deficiency in Patients on Long–Term Gastric–Tube Feeding: Estimation of Linoleic Acid and Long–Chain Unsaturated n–3 Fatty Acid Requirement in Man", Am. J. Clin. Nutr., vol. 5, 1987, pp 66–77.

Bjerve et al., "Alpha–Linoleic Acid Deficiency in Man: Effect of Ethyl Linolenate on Plasma and Erythrocyte Fatty Acid Composition and Biosynthesis of Prostanoids", Am. J. Clin. Nutr., vol. 46, 1987, pp 570–576.

Bogden et al., "Zinc and Immunocompetence in Elderly People: Effects of Zinc Supplementation for 3 Months", Am. J. Clin. Nutr., vol. 48, 1988, pp 655–663.

Bogden et al., "Zinc and Immunocompetence in the Elderly: Baseline Data on Zinc Nutriture and Immunity in Unsupplemented Subjects", Am. J. Clin. Nutr., vol. 46, 1987, pp 101–109.

Borum, "Role of Carnitine in Lipid Metabolism", Lipds in Modern Nutrition, New York: Raven Press, 1987, pp 51–58.

Borum et al., "Carnitine Content of Liquid Formulas and Special Diets", Am. J. Clin. Nutr., vol. 32, 1979, pp 2272–2276.

Breslow, "Nutrional Status and Dietary Intake of Patients with Pressure Ulcers: Review of Research Literature 1943 to 1989", Decubitus, vol. 4, No. 1, 1991, pp 16–21.

Brinson, "The Effect of Peptide–Based Diets on the Intestinal microcirculation in a Rat Model", Nutr. Clin. Prac., vol. 5, 1990, pp 238–240.

Brinson et al., "Diarrhea Associated with Severe Hypoalbuminemia: A Comparison of a Peptide–Based Chemically Defined Diet and Standard Enteral Alimentation", Critical Care Medicine, vol. 16, No. 2, 1988, pp 130–136.

Brinson et al., "Intestinal Absorption of Peptide Enteral Formulas in Hypoproteinemic (Volume Expanded) Rats: A Paired Analysis", Critical Care Medicine, vol. 17, No. 7, 1989, pp 657–660.

Bynoe et al., "Nutritional Support in Trauma Patients", Nutr. Clin. Prac., vol. 4, 1988, pp 137–144.

Cerra et al., "Enteral Nutrition in Hypermetabolic Surgical Patients", Critical Care Medicine, vol. 17, No. 7, 1989, pp 619–622.

Cerra et al., "The Effect of Stress Level, Amino Acid Formula, and Nitrogen Dose on Nitrogen Retention in Traumatic and Septic Stress", Ann. Surg., vol. 205, No. 3, 1987, pp 282–287.

Cerra et al., "What's New in Nutrition Support in Critical Care", Perspective in Clinical Nutrition, Kinney, Borum (Eds.), Urban & Schwarzenberg: Baltimore–Munich, 1989, pp 323–338.

Chandra, "Trace Element Regulation of Immunity anad Infection", J. of the American College of Nutrition, vol. 4, No. 1, 1985, pp 5–16.

Chernoff et al., "The Effect of a Very High–Protein Liquid Formula (Replete) on Decubitus Ulcer Healing in Long–Term Tube–Fed Institutionalized Patients", J. Am. Diet. Assoc., vol. 90, 1991.

Clintec Nutrition Company, Proper Nutrition for ICU Patients in Critical, Brochure 1994.

Clintec Nutrition Company, When you Creat Such a Unique Enteral Formula, It's Hard Not to Create Attention, Brochure, 1994.

Clintec Nutrion Company, Crucial Needs Require a Cucial Solution, Brochure 1994.

Clintec Nutrion Company, Crucial Compared to Perative, Brochure, 1995.

Clintec Nutrion Company, When Your First Choice Has to be Your Best Choice, Reabilan Brochure (Undated).

Clintec Nutrition Company, Reabilan HN, Brochure (Undated).

D–Atellis et al., "Branched–Chain Amino Acids", Nutrition in Critical Care, In Zaloga (ed.), St. Louis, MO: Mosby, 1994, pp 81–106.

Dominioni et al., "Enteral Feeding in Burn Hypermetabolism: Nutritional and Metabolic Effects of Different Levels of Calorie and Protein Intake", J. of Parenteral and Enteral Nutrion, vol. 9, No. 3, 1985, pp 269–279.

Dominioni et al., "Prevention of Severe Postburn Hypermetabolism and Catabolism by Immediate Intragastric Feeding", J. Burn Care Rehab., vol. 5, No. 2, 1984, pp 106–112.

Ehrlich et al., "Effects of Cortisone and Vitamin A on Wound Healing", Annals of Surgery, vol. 167, No. 3, 1968, pp 324–328.

Ehrlich et al., "Effects of Vitamin A and Glucocoricoids upon Inflammation and Collagen synthesis", Ann. Surg., vol. 177, No. 2, 1973, pp 222–227.

Ehrlich et al., "Effects of Beta–Carotene, Vitamin A, and Glucocorticoids on Collagen Synthesis in Wounds", Proc. Soc. Exp. Biol. Med., vol. 137, No. 1, 1971, pp 936–938.

Fabiani et al., "Oral Hyperalimentation in the Nutritional Management of Burned Patients", SAMJ, vol. 67, 1985, pp 768–770.

Freeman et al., "Effects of Magnesium Infusions on Magnesium and Nitrogen Balance During Parenteral Nutrition", The Canadian J. of Surgerey, vol. 25, No. 5, 1982, pp 570–574.

Geggel et al., "Nutritional Requirement for Taurine in Patients Receiving Long–Term parenteral Nutrition", The New England J. of Medicine, vol. 312, No. 3, 1985, pp 142–146.

Goodson et al., "Wound Healing", Nutrition and Metabolism in Patient Care, In: Kinney et al. (Eds.), Philadelphia, PA: WB Saunders, 1988, 635–642.

Gottschlich et al., "Enteral Nutrition in Patients with Burn or Trauma", Clinical Nutrition Enteral and Tube Feeding 2nd Edition, In: Rombeau et al. (Eds.), Philadelphia, PA: WB Saunders, 1990, pp 306–324.

Gottschlich et al., "Vitamin Supplementation in the Patient with Burns", J. Burn Care Rehab., vol. 11, No. 3, 1990, pp 275–279.

Granger et al., "Intestinal Absorption of Elemental and Standard Enteral Formulas in Hypoproteinemic (Volume Expanded) Rats", J. of Parenteral and Enteral Nutrition, vol. 12, No. 3, 1988, pp 278–281.

Greenberger et al., "Medium–Chain Triglycerides: Physiologic Considerations and Clinical Implications", The New England J. of Medicine, vol. 280, No. 19, 1969, pp 1045–1058.

Hadley et al., "Nutrion and Wound Healing", Top. Clin. Nutr., vol. 5, No. 4, 1990, pp 72–81.

Hallbrook et al., "Serum–Zinc and Healing of Venous Leg Ulcers", Lancet, 1972, pp 780–782.

Hayes, "Vitamin–Like Molecules (D) Taurine", Modern Nutrition in Health and Disease, 7th Edition, Philadelphia: Lea and Febiger, 1988, pp 464–470.

Heymsfield et al., "Respiratory, cardiovascular, and metabolic effects of enteral hyperlimentation: influence of formula dose and composition", The American J. of Clinical Nutrion, vol. 40, 1984, pp 116–130.

Holman, "Function and Biologic Activities of Essential Fatty Acids in Man", Fat Emulsion in Parenteral Nutrition, Chicago: American Medical Association, 1976, pp 5–14.

Holt, "Medium Chain Triglycerides: A Useful Adjunct in Nutritional Therapy", Gastroenterology, vol. 53, No. 6, 1967, pp 961–966.

Hunt, "Control of Wound Healing with Cortisone and Vitamin A", The Ultrastructure of Collagen, In: Longacre JJ (ed.), Springfield, IL: Charles C. Thomas, 1976, pp 497–508.

Hunt et al., "Effect of Vitamin A on Reversing the Inhibitory Effect of Cortisone on Healing of Open Wounds in Animals and Man", Annals of Surgery, vol. 170, No. 4, 1969, pp 633–641.

Hunt et al., "Selenium Depletion in Burn Patients", J. of Parenteral and Enteral Nutrition, vol. 8, No. 6, 1984, pp 695–699.

Ireton–Jones et al., "Nutrition for Adult Burn Patients: A Review", Nutr. Clin. Prac., vol. 6, No. 1, 1991, pp 3–7.

Jahoor et al., "Dynamics of the Protein Metabolic Response to Burn Injury", Metabolism, vol. 37, No. 4, 1988, pp 330–337.

Johnson et al., "Metabolism of Medium–Chain Triglyceride Lipid Emulsion", Nutrition International, vol. 2, No. 3, 1986, pp 150–158.

Joint FAO/WHO Ad Hoc Expert Committee, "Protein and Energy Requirements: A Joint FAO/WHO Memorandum", Bulletin of the World Health Organization, vol. 57, 1979, pp 65–79.

Kaunitz, "Clinical uses of medium–chain triglycerides", Drug Therapy, vol. 8, 1978, pp 91–96.

Kissilef et al., "Physiology of the Control of Food Intake", Ann. Rev. Nutr., vol. 2, 1982, pp 371–418.

Kubo et al., "Fluid and Electrolyte Problems of Tube–Fed Patients", Am. J. of Nursing, vol. 76, No. 6, 1976, pp 912–916.

Law et al., "The Effect of Dietary Protein Depletion on Immunocompetence: The Importance of Nutritional Repletion Prior to Immunologic Induction", Ann. Surgery, vol. 179, No. 2, 1974, pp 168–173.

Levenson, "Micronutrients (Vitamins, Trace Minerals)", In ASPEN Program Manual of Proceedings of the 16th Clinical Congress, 1992, pp 189–198.

Long et al., "Metabolic Response to Injury and Illness: Estimation of Energy and Protein Needs from Indirect Calorimetry and Nitrogen Balance", J. of Parenteral and Enteral Nutrition, vol. 3, No. 6, 1979, pp 452–456.

Mahan et al., "The Assesment of Nutritional Status", Krause's Food and Nutrion & Diet Therapy, 8th Edition, Philadelphia: WB Saunders Company, 1992, pp 293–313.

Mandt et al., "Nutronal Requirements", Nutrition Support Handbook, In: Teasley–Strausberg (ed.), Cincinnati, OH: Harvey Whitney Books Co., 1992, pp 19–36.

Mascioli et al., "Intravenous Infusion of a Physical Mixture of Medium and Long Chain Triglyceride Emulsion", Clin. Res., vol. 33, 1985, 275A.

McClave et al., "Immunonutrition and Enteral Hyperlimentation of Critically Ill Patients," Digestive Diseases and Sciences, vol. 37, No. 8, 1992, pp 1153–1161.

Mead Johnson, Metabolic and Nutrion Support for Trauma and Burn Patients, A Symposium, Abstracts, 1982, pp 1–13.

Meredith et al., "Visceral Protein Levels in Trauma Patients are Greater with Peptide Diet than with Intact Protein Diet," The J. of Trauma, vol. 30, No. 7, 1990, pp 825–829.

National Research Council, "Recommended Dietary Allowances, 10th Edition," Washington, DC: National Academy Press, 1989.

Nichols et al., "Magnesium Suplementation in Protein–Calorie Malnutrition", The American J. of Clinical Nutrition, vol. 13, 1978, pp 176–188.

Nutritional Care of Metabolically Stressed Patients, Proceedings from the Metabolic and Nutrion Support for Trauma and Burn Patients Symposium, White Sulphur Springs, West Virginia, 1983, pp 1–77.

Ortiz et al., "A Comparative Post–Operative Study—An Enteral Solution Based on Free Amino Acids", Gastroenterologic Clinique et Biologique, vol. 9, No. 2, 1985, pp 182–183.

Pearson et al., "An Estimation of the Potassium Requirements for Equilibrium in Burned Patients", Surgery Gynecology and Obstetrics, vol. 112, No. 3, 1961, pp 263–273.

Poriest et al., "Acceleration of Wound Healing in Man with Zinc Sulphate Given by Mouth", Lancet, 1967, pp 121–124.

Prasad et al., "Serum Thymulin in Human Zinc Deficiency", J. Clin. Invest., vol. 82, 1988, pp 1202–1210.

Principles of Nutritional Support: Proceedings from the Metabolic and Nutrition Support for Trauma and Burn Patients Symposium, White Sulphur Springs, West Virginia, 1982, pp 1–25.

Randall et al., "Randomized Clinical Trial in Hospitalized Patients Using Intravenous Medium Chain Triglyceride Emulsions", Clin. Res., vol. 33, 1985, 276A.

Ringsdorf et al., "Vitamin C and Human Wound Healing", Oral Surgery, vol. 53, No. 3, 1982, pp 231–236.

Ross et al., "Wound Healing and Collagen Formation—II. Fine Structure in Experimental Scurvy", The J. of Cell Biology, vol. 12, 1962, pp 533–551.

Ross et al., "Wound Healing and Collagen Formation—V. Quantitative Electron Microscope Radioautographic Observations of Prolin–H Utilization by Fibroblasts", The J. of Cell Biology, vol. 27, 1965, pp 83–106.

Ross et al., "Vitamin A as a Hormone: Recent Advances in Understanding the Actions of Retinol, Retinoic Acid, and Beta Carotene", J. of the American Dietetic Ass., vol. 93, No. 11, 1993, pp 1285–1290.

Ross Laboratories Brochure, Specilized Elemental Nutrion with Glutamine—The Role of ALITRAQ Specialized Elemental Nutrion with Glutamine, 1991.

Ross Laboratories Brochure, Introducing ALITRAQ Specialized Elemental Nutrition with Gluamine, 1992.

Saller et al., "Medium Chain Triglycerides in Parenteral Nutrition", J. of Parenteral and Eneteral Nutrition, vol. 5, No. 2, 1981, pp 115–119.

Sandoz Nutrition Brochure, IMPACT, 1993.

Sandoz Nutrition Brochure, Introducing Impact, 1989.

Sandoz Nutrition Brochure, IMPACT, 1991.

Sandstead et al., "Zinc and Wound Healing: Effects of Zinc Deficiency and Zinc Supplementation", The Am. J. of Clinical Nutrition, vol. 23, No. 5, 1970, pp 514–519.

Silk, "Nutritional Support in Hospital Practice", Oxford, Blackwell Scientific Publications, 1983, pp 79–82.

Simopoulos, "Omega–3 Fatty Acids in Health and Disease and in Growth and Development", Am. J. Clin. Nutr., vol. 54, 1991, pp 438–463.

Spiller et al., "Malabsorption", Nutrition and Metabolism in Patient Care, Kinney et al., (Eds.), Philadelphia, PA: WB Saunders, 1988, pp 281–304.

Stotts et al., "Nutrition: A Critical Component of Wound Healing", AACN Clin. Issues, vol. 1, No. 3, 1990, pp 585–594.

Sturman et al., "The Biology of Taurine in Nutrition and Development", Adv. Nutr. Res., vol. 3, 1980, pp 231–299.

Sucher, "Medium Chain Triglycerides: A Review of Their Enteral Use in Clinical Nutrition", Nutrition in Clinical Practice, 1986, pp 146–150.

Symposium Highlights Metabolic and Nutrition Support for Trauma and Burn Patients, White Sulphur Springs, West Virginia, 1982, pp 1–26.

Szebeni et al., "Vitamin A Levels in the Serum of Burned Patients," Burns, vol. 7, No. 5, 1981, pp 313–318.

TraumaCal, Feeding the Hypermetabolic Patient, Clinical Experience, A Symposium, 1983, pp 1–74.

Twyman et al., "High Protein Enteral Feedings: A Means of Achieving Positive Nitrogen Balance in Head Injured Patients," J. of Parenteral and Enteral Nutrition, vol. 9, No. 6, 1985, pp 679–684.

Waxman et al., "Protein Loss Across Burn Wounds", The J. of Trauma, vol. 27, No. 2, 1987, pp 136–140.

Ziegler et al., "Efficiency of Enteral Nitrogen Support in Surgical Patients: Small Peptides v. Non–Degraded Proteins", Gut, vol. 31, 1990, pp 1277–1283.

* cited by examiner

CALORICALLY DENSE NUTRITIONAL COMPOSITION

This application is a continuation of 09/025,363 filed Feb. 18, 1998.

BACKGROUND OF THE INVENTION

The present invention relates generally to the treatment and nutritional support of patients. More specifically, the present invention relates to compositions for use in metabolically stressed patients who need food restriction, but who do not necessarily need increased contents of protein or special nutrients.

Patients suffering from a loss of nutrients require adequate nutritional support. A lack of adequate nutritional support can result in malnutrition associated complications. Thus, the goal of nutritional support is to maintain body mass, provide nitrogen and energy in adequate amounts to support healing, meet metabolic demands characterized by the degree of stress, and support immune function.

A traditional form of nutritional support is administering whole protein liquid feedings to the patient to remedy the protein deficiency. However, some patients requiring nutritional support have a compromised absorptive capacity and thus cannot tolerate whole protein liquid feedings as well as the long-chain fatty acids and complex carbohydrates often present in such whole protein feedings. Many diseases or their consequences can cause malabsorption by impairment of either digestion or absorption. For instance, patients suffering from various types of inflammatory bowel diseases typically cannot tolerate whole protein feedings. As a result, semi-elemental and elemental protein diets were developed to treat such compromised patients.

However, in addition to the traditional inflammatory bowel type patients, semi-elemental and elemental protein diets are currently being used in other patient segments. Specific conditions where these diets are being used include, for example, total parenteral nutrition patients receiving early transitional feedings, acutely ill, and catabolic patients with increased nitrogen needs yet requiring an elemental diet.

Still further, many patients suffering from metabolic stress have a significant need for increased energy but often do not need or tolerate protein levels beyond the normal requirement. Such patients also cannot tolerate the food volume necessary to deliver the energy they need. As a result, such patients need an elemental diet that provides calorically dense nutritional support while at the same time providing moderate non-protein calories per gram of nitrogen. Although a variety of elemental and semi-elemental diets are currently being used in an attempt to treat and/or provide nutritional requirements to such patients, the inventors of the present invention do not believe the needs of the metabolic stressed patients are being adequately met.

Accordingly, a need exists for an enteral nutritional formulation that meets the nutrient requirements of metabolically stressed patients without unnecessarily subjecting such patients to high fluid volume treatments or formulations with increased protein levels.

SUMMARY OF THE INVENTION

The present invention provides a nutritional composition designed for metabolically stressed patients. To this end, the present invention provides nutritional support with formulations containing increased caloric density without elevated protein levels or excess fluid.

Pursuant to the present invention, an enteral composition includes a protein source comprising approximately 15% to 20% of the caloric distribution of the composition; a carbohydrate source; and a lipid source including a mixture of medium and long chain triglycerides. Significantly however, the enteral composition, unlike prior compositions, has a caloric density of at least approximately 1.4 kcal/mL.

In an embodiment, the hydrolyzed protein source is essentially 100% hydrolyzed whey protein.

In another embodiment, the lipid source of the composition includes at least 70% medium chain triglycerides.

Still further, in another embodiment, the enteral composition of the present invention uniquely provides calorically dense nutritional support while at the same time providing moderate non-protein calories per gram nitrogen (NPC/gN). Specifically, the present invention uniquely provides an enteral composition having a clinically acceptable ratio of non-protein calories per gram nitrogen of at least approximately 90:1; for example about 140:1 to about 100:1.

Moreover, due to the calorically dense nature of the composition of the present invention, the composition includes 100% of U.S. RDA vitamins & minerals in approximately 1500 kcal (1000 mL).

The present invention also provides a method for providing nutrition to a metabolically stressed patient. The method includes administering to the patient a therapeutically effective amount of a composition having a caloric density of at least approximately 1.4 kcal/mL. The composition with such increased caloric density includes a protein source comprising approximately 15% to 20% of the calorie distribution of the composition, a carbohydrate source, and a lipid source including a mixture of medium and long chain triglycerides.

An advantage of the present invention is that it provides a nutritional composition that is ready-to-use, nutritionally complete, and contains proteins, lipids, vitamins and minerals in proportions suitable for older children (10+ years) and adults.

Moreover, an advantage of the present invention is that it provides a nutritional diet for tube as well as oral use designed for optimal tolerance and absorption in metabolically stressed patients.

Another advantage of the present invention is that it provides a composition containing hydrolyzed whey protein, medium chain triglycerides and maltodextrin to enhance absorption in metabolically stressed patients.

Yet another advantage of the present invention is that it provides calorically dense nutritional support in the form of an elemental diet while at the same time providing a moderate NPC/gN ratio (non-protein calories per gram nitrogen) of greater than at least approximately 90:1; for example about 140:1 to about 100:1.

Still further, an advantage of the present invention is the high caloric density will be especially useful for patients using the composition as a supplement (i.e. HIV, cystic fibrosis) and as a nocturnal feeding (cystic fibrosis).

Additional features and advantages of the present invention are described in, and will be apparent from, the detailed description of the presently preferred embodiments.

DETAILED DESCRIPTION OF THE PRESENTLY PREFERRED EMBODIMENTS

Nutritional support of hospitalized as well as non-hospitalized patients requires prevention, recognition and treatment of nutritional depletion that may occur with illness. The goals of nutritional support include stabilizing metabolic state, maintaining body mass, and/or facilitating growth in the presence of disease and gastrointestinal dysfunction.

Certain disease states exist that alter intake, absorption or metabolism. For example, certain health conditions can impair the nutrient absorption and/or reduced gastrointestinal tolerance for diets which are based on whole proteins. These conditions include patients suffering specifically from a compromised gut function as well as patients, due to the severity of their condition, who are simply unable to tolerate whole protein diets.

Moreover, although certain patients with impaired nutrient absorption and/or reduced gastrointestinal tolerance may need fluid restriction, such patients do not necessarily need the increased contents of protein or special nutrients often present in existing elemental diets. For instance, patient groups suffering from Crohn's disease, cancer, cystic fibrosis, short bowel syndrome, cerebral palsy, intractable diarrhea, gastric reflux and HIV/AIDS often are classified as falling within this group of patients. Likewise, patients transitioning from parenteral feeding, are acutely ill, or are considered post-surgery with cardiac/renal complications requiring fluid control also have a need for increased energy, but often do not need or tolerate protein levels beyond normal requirements and cannot tolerate the fluid volume necessary to deliver the needed energy. For purposes of the present application, this population of patients are generically referred to as metabolically stressed patients.

The present invention provides a product that is specifically directed to meet the nutritional needs of metabolically stressed patients without elevated protein levels or excess fluid. To this end, the present invention provides calorically dense nutritional support in the form of an elemental diet while at the same time providing a moderate NPC/gN ratio. The nutritional diet of the present invention preferably utilizes hydrolyzed whey protein, medium chain triglycerides and maltodextrin to enhance absorption in the metabolically stressed patients.

The protein source of the present invention provides approximately 15% to 20% of the total calories of the composition. In an embodiment, the protein source comprises approximately 16% (4 g/100 kcal) of the total calories of the composition. For adults and older children (10+ years old), the protein concentration of the present invention is optimal for the moderate tissue repair needs of the targeted patient populations without imposing an undue nitrogen burden on renal function.

The composition of the present invention is preferably a peptide-based diet. In choosing the protein source, the present invention maximizes tolerance and absorption with the use of a hydrolyzed protein. In an embodiment, the protein source is enzymatically hydrolyzed whey protein. In a preferred embodiment, the protein source is essentially 100% hydrolyzed whey protein. This type of protein source reduces the incidence of gastric reflux because gastric emptying is faster than with diets containing casein or whole whey.

Also, the hydrolyzed whey protein of the present invention serves as a rich source of the amino acid cysteine. Cysteine is a limiting amino acid for the formation of glutathione, and endogenous glutathione needs are greater in patients with chronic inflammatory and infectious conditions. The formula of the present invention preferably contains approximately 0.1% to 0.8% of calories as cysteine. In a preferred embodiment, the formula contains approximately 0.37% of calories as cysteine (925 mg/1000 calories).

The protein source may also include a portion as free amino acids. As with protein hydrolysate, the use of free amino acids reduces the potential for nutrient malabsorption. In an embodiment, the protein source contains from about 0.1% to 2.0% free amino acids. Preferably, the protein source of the present invention contains less than about 2% free amino acids.

Carbohydrates provides, in an embodiment, approximately 35% to 65% and, most preferably, approximately 40% to 60% of the caloric content of the composition. In an embodiment, the carbohydrate source is approximately 51% of the caloric content of the composition. A number of carbohydrates can be used pursuant to the present invention. By way of example, the carbohydrates can be chosen from maltodextrin, corn starch, sucrose and corn syrup solids.

The lipid source of the present invention includes a mixture of medium chain triglycerides (MCT) and long chain triglycerides (LCT). The lipid source of the present invention is approximately 20% to about 50% of the caloric content of the total composition; preferably about 25% to about 40%. In an preferred embodiment, the lipid source is approximately 33% of the caloric content of the composition.

The lipid profile is designed to meet essential fatty acid needs (omega-3 and omega-6) while also keeping medium-chain triglyceride (MCT) content high and long-chain triglyceride (LCT) content low compared with prior formulas. Preferably, the lipid source comprises approximately 30% to 80% by weight MCTs. In a preferred embodiment, the lipid source of the present invention includes about 70% by weight from MCTs. Such MCTs are easily absorbed and metabolized in the metabolically stressed patient. The use of MCTs will also reduce the risk of potential for nutrient malabsorption. In a preferred embodiment, the medium chain triglyceride source is fractionated coconut oil.

The remainder of the lipid source is a mixture of LCTs. Suitable sources of long chain triglycerides are canola oil, corn oil, soy lecithin and residual milk fat and soybean oil. Pursuant to the present invention, the lipid profiles containing such LCTs are designed to have a polyunsaturated fatty acid omega-6 (n-6) to omega-3 (n-3) ratio of approximately 1:1 to 10:1; preferably about 6:1 to about 9:1. The proposed ratio of n-6:n-3 is designed to reduce the immune suppression associated with high omega-6 fatty acid concentration and provide adequate essential fatty acid. In an embodiment, the composition includes an omega-6 to omega-3 ratio of approximately 7:1.

Still further, the composition of the present invention contains a specialized vitamin and mineral profile. The composition includes at least 100% of the United States Recommended Daily Allowance (USRDA) of vitamins and minerals in 1500 kcal. Moreover, the composition includes higher levels of key vitamins and minerals designed to support the metabolically stressed patients.

Specifically, pursuant to the present invention, the composition includes a high level of zinc. Preferably, at least approximately 225% of the USRDA of zinc is provided in the composition per 1500 Kcal. In an embodiment, 28.5 to 43.5 mg per 1500 calories of zinc are provided. In a preferred embodiment, 36 mg per 1500 calories of zinc is provided. The increased zinc compensates for zinc losses and provides increased zinc for tissue repair in a patient having increased healing requirements.

The composition of the present invention also includes an increased amount of vitamin C. At least approximately 750% of the USRDA of vitamin C is provided per 1500

Kcal. In an embodiment, 405 to 615 mg per 1500 calories of vitamin C is provided. In a preferred embodiment, 510 mg per 1500 calories of vitamin C is provided. Vitamin C is believed to accelerate the healing and granulation in patients with severe healing requirements. Vitamin C will support increased requirements/losses after surgery.

Pursuant to the present invention, the composition also includes increased amounts of selenium. Selenium deficiencies may develop in patients having elevated healing requirements. Pursuant to the present invention, at least approximately 60 to 90 mcg of selenium are provided in 1500 calories of formula. In a preferred embodiment, approximately 75 mcg of selenium per 1000 calories is provided.

Many of the commercially available enteral formulas contain far below the amount of carotenoids (beta-carotene) found in usual diets of normal healthy people. In fact, patients on liquid formula diets as their sole source of nutrition for one week or more have been found to have plasma concentrations of carotenoids of only 8% to 18% as compared to controls consuming a free choice of diet. Bowen et al, "Hypocarotenemia in Patients Fed Enterally with Commercial Liquid Diets," *Journal of Parenteral and Enteral Nutrition*, 12(5): 44–49 (1988). Those on enteral formulas for more than three weeks have negligible concentrations of any common serum carotenoids.

To meet these requirements, the present invention includes a source of beta-carotene. Beta-carotene is added to the composition to normalize beta-carotene serum plasma levels and to avoid beta-carotene deficiency in long term tube-fed patients. Beta-carotene also meets a portion of the required Vitamin A, thereby meeting micro-nutrient requirements in a small caloric volume. Moreover, beta-carotene is an important nutrient with anti-oxidant properties. The composition includes approximately 1.25 to 4.0 mg per 1500 kcal. In a preferred embodiment, the composition includes approximately 1.52 mg of beta-carotene per 1500 kcal of the composition. This amount prevents deficiencies and provides for possible increased requirements in the healing patient. Moreover, the beta-carotene and vitamin A levels allow plasma concentrations of retinol to be increased to near normal optimal levels of 500 mcg per liter.

The present invention also provides increased amounts of L-carnitine and taurine to support the increased requirements of the acutely ill, catabolic patient. Both taurine and L-carnitine are preferably present in amounts of approximately 120 to 180 mg per 1500 calories. In preferred embodiments, both taurine and L-carnitine are present in an amount of approximately 150 mg per 1500 calories.

Still further, the composition of the present invention includes decreased amounts of magnesium. Magnesium has been associated with diarrhea. In an embodiment, magnesium is present in an amount of approximately 308 mg to 462 mg per 1500 calories. In a preferred embodiment, magnesium is present in an amount of approximately 400 mg per 1500 calories.

The composition of the present invention is a ready-to-use enteral formulation. The composition can provide the total nutritional requirements of the metabolically stressed patient or can act as a supplement. The composition can be tube-fed to a patient, or fed by having the patient drink same. For instance, the composition can be provided in cans or a spike and hang bag. The composition is preferably ready to use and does not require reconstitution or mixing prior to use.

Unlike prior formulations, the present invention provides calorically dense nutritional support in the form of a elemental diet while at the same time providing a moderate NPC/gN ratio. To this end, the present invention preferably has a caloric density of approximately 1.4 to 1.8 kcal/mL. For example, the composition of the present invention has a caloric density of about 1.5 kcal/ml. The composition provides a moderate NPC/gN ratio of at least about 90:1. For example, the composition provides a NPC/gN ratio of about 140:1 to about 100:1. Preferably, the composition provides a NPC/gN ratio of 131:1.

Furthermore, unlike prior formulations, the present invention has a low osmolality of approximately 375 to 600 mOsm/kg $H_2O$ in an unflavored product. The osmolality of the composition in a flavored product is approximately 500 to 700 mOsm/kg $H_2O$.

The composition of the present invention may be utilized to treat metabolically stressed patients. As used herein, metabolically stressed patients are patients who, due to either a disorder or condition, are unable to tolerate whole protein diets and need fluid restriction, while at the same time cannot tolerate elevated protein levels or excess fluid. For example, the present invention may be utilized to provide nutrition to critically ill patients transitioning from total parenteral nutrition therapy and acutely ill, catabolic patients. Moreover, the present invention can be utilized to provide nutrition to patients suffering from the following conditions and/or diseases; Crohn's disease; cystic fibrosis; HIV/AIDS; cancer; patients of post-surgery with cardiac/renal complications requiring fluid control; intractable diarrhea; short bowel syndrome; cerebral palsy; and gastric reflux.

Of course, it will be appreciated that a variety of formulations are possible in accordance with the present invention. An example of a formulation in accordance with the present invention has a caloric density of about 1.5 kcal/ml. This is equivalent to 375 kcal/250 ml which will, in a preferred embodiment, be one unit (can or container) of product.

By way of example, and not limitation, an example of the suitable composition that may be used pursuant to the present invention is as follows.

The composition includes the following ingredients: water; maltodextrin, enzymatically hydrolyzed whey protein, medium-chain triglycerides (MCT source: fractionated coconut oil); corn starch; soy bean oil; soy lecithin; potassium phosphate; guar gum; calcium citrate; sodium phosphate; choline chloride; sodium chloride; calcium phosphate; calcium ascorbate; magnesium chloride; potassium citrate; magnesium oxide; potassium chloride; taurine; citric acid; L-carnitine; zinc sulfate; ferrous sulfate; DL-alpha tocopherylacetate; nicotinamide; retinyl palmitate; calcium pantothenate; manganese sulfate; copper sulfate; pyridoxine hydrochloride; riboflavin; thiamine; folic acid; cholecal ciferol; biotin; potassium iodide; beta-carotene; sodium molybdate; chromium chloride; phylloquinone; sodium selenate; and cyanocobalamin.

The composition of the present invention may have the following nutrient composition (per 1500 calories (1000 ml)):

| Nutrient Composition | Amount | % U.S. RDA* |
|---|---|---|
| Protein | 60.0 g | 132 |
| Carbohydrate | 191.0 g | ** |
| Lipid*** | 58.5 g | ** |
| Water | 780 mL | ** |

-continued

| Nutrient Composition | Amount | % U.S. RDA* |
|---|---|---|
| Vitamin A | 6000 IU | 100 |
| Beta-Carotene | 3.0 mg | ** |
| Vitamin D | 600 IU | 148 |
| Vitamin E | 45 IU | 148 |
| Vitamin K | 75 mcg | ** |
| Vitamin C | 510 mg | 840 |
| Thiamine ($B_1$) | 3.0 mg | 200 |
| Riboflavin ($B_2$) | 3.6 mg | 212 |
| Niacin | 42 mg | 208 |
| Vitamin $B_6$ | 6 mg | 300 |
| Folic Acid | 810 mcg | 136 |
| Pantoth. Acid | 21 mg | 140 |
| Vitamin $B_{12}$ | 12 mcg | 132 |
| Biotin | 600 mcg | 132 |
| Choline | 675 mg | ** |
| Taurine | 150 mg | ** |
| L-Carnitine | 150 mg | ** |
| Calcium | 1000 mg | 100 |
| Phosphorus | 1000 mg | 100 |
| Magnesium | 400 mg | 100 |
| Zinc | 36 mg | 240 |
| Iron | 27 mg | 148 |
| Copper | 3.0 mg | 148 |
| Manganese | 4.0 mg | ** |
| Iodine | 225 mcg | 148 |
| Sodium | 1020 mg | ** |
| Potassium | 1872 mg | ** |
| Chloride | 1740 mg | ** |
| Chromium | 60 mcg | ** |
| Molybdenum | 180 mcg | ** |
| Selenium | 75 mcg | ** |

*U.S. Recommended Daily Allowance for Adults & Children 4 or more years of age
**U.S. RDA not established
***MCT provides 40.8 grams/1000 ml In this example, the protein source comprises essentially 100% hydrolyzed whey protein. The carbohydrate source preferably includes approximately 70% to 95% maltodextrin, from about 5% to 15% corn starch, and up to about 20% sucrose; all % being on the basis of energy. Lastly, the lipid source preferably includes approximately 70% MCTs, approximately 17% soybean oil; approximately 8% residual milk fats; and approximately 5% soy lecithin; all % being on the basis of energy.

By way of example, and not limitation, a contemplative example illustrating the use of the present invention will now be given.

CONTEMPLATIVE EXAMPLE

An experimental enteral product formulated according to the principles presented in this application and essentially identical to the composition presented can be evaluated in a group of severely traumatized patients requiring early enteral feeding. Patients are fed by small bowel feeding tubes. The goal of this early feeding is to supply at least 60% of their calculated energy needs. The primary data collected to evaluate this early feeding is to determine the tolerance to early and fairly aggressive feeding. Gastrointestinal symptoms such as diarrhea, bloating and cramping are tabulated and evaluated. Actual intake as a percentage of calculated energy requirements is calculated for each patient on each day of feeding for five consecutive days. The nutritional goals set are 25 kcal/kg of estimated body weight/day and 1.6 grams of protein/kg/day.

Eighteen (18) patients, for example, are entered into the study and 16 of these patients complete the 5 days of feeding. For the first 24 hours of feeding, the average intake for the 16 patients is 65±12% of the calculated nutritional requirement. The intake over the first 48 hours of feeding is 68±8% of requirements. Over the first 72 hours of feeding, the average intake is 73±6% of requirements and for the first 96 hours of feeding, the mean intake typically rises to 87±6% of requirement. Over the full five days of feeding evaluation, the average intake is 92±7% of the calculated energy requirements for the 16 patients who completed the full study period. Diarrhea develops in only one patient in the group and this generally persists for approximately 18 hours. No other gastrointestinal symptoms would typically be reported during the study period.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. An enteral, peptide-based composition comprising:
a protein source consisting of enzymatically hydrolyzed whey and free amino acids wherein the protein source provides approximately 15% to 18% of energy of the composition, and wherein said protein source is the sole protein source of the composition;
a carbohydrate source; and
a lipid source including a mixture of medium and long chain triglycerides, the enteral composition having a caloric density of 1.4 kcal/mL to 1.8 kcal/mL, wherein the composition provides a ratio of non-protein calories per gram nitrogen of at least 90:1.

2. The enteral composition of claim 1 wherein the lipid source comprises approximately 20% to 50% of the calorie distribution of the composition.

3. The enteral composition of claim 1 including 100% of U.S. RDA of vitamins and minerals in approximately 1500 kcal.

4. The enteral composition of claim 1 wherein the composition includes per 1500 kcal of composition:
a zinc source providing from approximately 28.5 to 43.5 mg;
a vitamin C source providing from approximately 405 to 615 mg;
a selenium source providing from approximately 60 to 90 mg;
a taurine source providing from approximately 120 to 180 mg; and
a L-carnitine source providing from approximately 120 to 180 mg.

5. The enteral composition of claim 1 further including a source of beta-carotene.

6. A method for providing nutrition to a metabolically stressed patient comprising the step of administering to the patient a therapeutically effective amount of an enteral, peptide-based composition comprising:
a protein source comprising approximately 15% to 18% of the calorie distribution of the composition, the protein source consisting of enzymatically hydrolyzed whey and free amino acids, and wherein said protein source is the sole protein source of the composition;
a carbohydrate source;
a lipid source;
the enteral composition having a caloric density of 1.4 kcal/mL to 1.8 kcal/mL; and the composition provides a ratio of non-protein calories per gram nitrogen of at least approximately 90:1.

7. The method of claim 6 wherein the lipid source comprises approximately 20% to 50% of the calorie distribution of the composition.

8. The method of claim 6 wherein the composition includes 100% of U.S. RDA of vitamins and minerals in approximately 1500 kcal.

9. The method of claim 6 wherein the composition is fed through a tube to the patient.

10. The method of claim 6 wherein the composition contains approximately 0.37% of the calories as cysteine.

11. The method of claim 6 wherein the composition includes per 1500 kcal of composition:
  a zinc source providing from approximately 28.5 to 43.5 mg;
  a vitamin C source providing from approximately 405 to 615 mg;
  a selenium source providing from approximately 60 to 90 mg;
  a taurine source providing from approximately 120 to 180 mg; and
  a L-carnitine source providing from approximately 120 to 180 mg.

12. The method of claim 6 wherein the composition further includes a source of beta-carotene.

13. An enteral, peptide-based composition for a metabolically stressed patient comprising:
  about 15% to 18% of the calorie distribution of the composition including a protein source consisting of enzymatically hydrolyzed whey and free amino acids, and wherein said protein source is the sole protein source of the composition;
  a carbohydrate source comprising at least 35% of the composition;
  a lipid source comprising at least 20 by weight of the composition; and
  the composition having a caloric density of 1.4 kcal/mL to 1.8 kcal/mL and a ratio of non-protein calories per gram of nitrogen of at least about 90:1.

14. The enteral composition of claim 13 which includes, per 1500 kcal:
  a zinc source providing from about 28.5 to about 43.5 mg zinc;
  a vitamin C source providing about 405 to 615 mg vitamin C;
  a selenium source providing about 60 to about 90 mg selenium;
  a taurine source providing about 120 to about 180 mg taurine; and
  a L-carnitine source providing about 120 to about 180 mg L-carnitine.

15. The enteral composition of claim 13 wherein the composition further comprises from about 0.1% to 2.0% free amino acids.

16. The enteral composition of claim 13 including at least 0.1% free amino acid.

17. A method for providing nutrition to a metabolically stressed patient comprising the step of administering to the patient a therapeutically effective amount of an enteral, peptide-based composition comprising:
  a protein source comprising approximately 15% to 18% of the calorie distribution of the composition, the protein source consisting of enzymatically hydrolyzed whey and free amino acids, and wherein said protein source is the sole protein source of the composition;
  a carbohydrate source;
  a lipid source;
  the enteral composition having a caloric density of 1.4 kcal/mL to 1.8 kcal/mL; and
  the composition provides a ratio of non-protein calories per gram nitrogen of at least approximately 90:1 wherein the composition includes at least 0.1% free amino acids.

* * * * *

(12) EX PARTE REEXAMINATION CERTIFICATE (10395th)
United States Patent
Mark et al.

(10) Number: US 6,849,595 C1
(45) Certificate Issued: Nov. 12, 2014

(54) CALORICALLY DENSE NUTRITIONAL COMPOSITION

(75) Inventors: David A. Mark, Oak Park, IL (US); Diana Twyman, Chicago, IL (US); Tom Michalski, Grayslake, IL (US)

(73) Assignee: Nestec S.A., Vevey (CH)

Reexamination Request:
No. 90/012,759, Dec. 31, 2012

Reexamination Certificate for:
Patent No.: 6,849,595
Issued: Feb. 1, 2005
Appl. No.: 09/759,037
Filed: Jan. 10, 2001

Related U.S. Application Data

(63) Continuation of application No. 09/025,363, filed on Feb. 18, 1998, now Pat. No. 6,200,950.

(51) Int. Cl.
*A23L 1/30* (2006.01)
*A23L 1/302* (2006.01)
*A23L 1/304* (2006.01)
*A23L 1/29* (2006.01)

(52) U.S. Cl.
USPC ............ 514/1.1; 514/17.7; 514/23; 514/474; 514/494; 514/547; 424/600; 424/641; 424/681; 424/72

(58) Field of Classification Search
None
See application file for complete search history.

(56) References Cited

To view the complete listing of prior art documents cited during the proceeding for Reexamination Control Number 90/012,759, please refer to the USPTO's public Patent Application Information Retrieval (PAIR) system under the Display References tab.

*Primary Examiner* — Dwayne Jones

(57) ABSTRACT

The present invention provides an enteral composition and method for providing nutrition to metabolically stressed patients. Pursuant to the present invention, the enteral composition has an increased caloric density of approximately 1.4 to 1.8 kcal/mL. The enteral composition includes a peptide based protein source, a lipid source, and a carbohydrate source.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 4 and 6 are cancelled.

Claims 2, 3, 5, 7-13 and 17 are determined to be patentable as amended.

Claims 14-16, dependent on an amended claim, are determined to be patentable.

2. The enteral composition of claim [1] *13* wherein the lipid source comprises approximately 20% to 50% of the calorie distribution of the composition.

3. The enteral composition of claim [1] *13* including 100% of U.S. RDA of vitamins and minerals in approximately 1500 kcal.

5. The enteral composition of claim [1] *13* further including a source of beta-carotene.

7. The method of claim [6] *17* wherein the lipid source comprises approximately 20% to 50% of the calorie distribution of the composition.

8. The method of claim [6] *17* wherein the composition includes 100% of U.S. RDA of vitamins and minerals in approximately 1500 kcal.

9. The method of claim [6] *17* wherein the composition is fed through a tube to the patient.

10. The method of claim [6] *17* wherein the composition contains approximately 0.37% of the calories as cysteine.

11. The method of claim [6] *17* wherein the composition includes per 1500 kcal of composition:

a zinc source providing from approximately 28.5 to 43.5 mg;

a vitamin C source providing from approximately 405 to 615 mg;

a selenium source providing from approximately 60 to 90 mg;

a taurine source providing from approximately 120 to 180 mg; and a L-carnitine source providing from approximately 120 to 180 mg.

12. The method of claim [6] *17* wherein the composition further includes a source of beta-carotene.

13. An enteral, peptide-based, *flavored* composition for a metabolically stressed patient comprising:

about 15% to 18% of the calorie distribution of the composition including a protein source consisting of enzymatically hydrolyzed whey and free amino acids, and wherein said protein source is the sole protein source of the composition;

a carbohydrate source comprising at least 35% of the composition;

a lipid source comprising at least 20% by weight of the composition; and the composition having a caloric density of 1.4 kcal/mL to 1.8 kcal/mL, a ratio of non-protein calories per gram of nitrogen of at least about 90:1, *and an osmolality of 500 to 700 mOsm/kg water*.

17. A method for providing nutrition to a metabolically stressed patient comprising the step of administering to the patient a therapeutically effective amount of an enteral, peptide-based, *flavored* composition comprising:

a protein source comprising approximately 15% to 18% of the calorie distribution of the composition, the protein source consisting of enzymatically hydrolyzed whey and free amino acids, and wherein said protein source is the sole protein source of the composition;

a carbohydrate source *comprising at least 35% of the composition*;

a lipid source *comprising at least 20% by weight of the composition*;

the enteral composition having a caloric density of 1.4 kcal/mL to 1.8 kcal/mL; and the composition provides a ratio of non-protein calories per gram nitrogen of at least approximately 90:1 wherein the composition includes at least 0.1% free amino acids, *and an osmolality of 500 to 700 mOsm/kg water*.

* * * * *